(12) United States Patent
Shefer et al.

(10) Patent No.: US 7,214,382 B2
(45) Date of Patent: May 8, 2007

(54) SELF-WARMING OR SELF-HEATING COSMETIC AND DERMATOLOGICAL COMPOSITIONS AND METHOD OF USE

(76) Inventors: Adi Shefer, 14 Jason Dr., East Brunswick, NJ (US) 08816; Samuel David Shefer, 14 Jason Dr., East Brunswick, NJ (US) 08816

( * ) Notice: Subject to any disclaimer, the term of this patent is extended or adjusted under 35 U.S.C. 154(b) by 0 days.

(21) Appl. No.: 10/454,915

(22) Filed: Jun. 5, 2003

(65) Prior Publication Data

US 2004/0253198 A1 Dec. 16, 2004

(51) Int. Cl.
*A61Q 19/00* (2006.01)

(52) U.S. Cl. .......................... 424/401; 424/59; 424/65; 424/69; 424/73; 424/78.03

(58) Field of Classification Search ................ 424/401, 424/70.1, 70.2, 73, 443
See application file for complete search history.

(56) References Cited

U.S. PATENT DOCUMENTS

| | | | |
|---|---|---|---|
| 3,250,680 A | 5/1966 | Menkart et al. ............... 167/85 |
| 3,439,088 A | 4/1969 | Edman ......................... 424/63 |
| 3,740,422 A * | 6/1973 | Hewitt ....................... 424/78.3 |
| 3,818,105 A | 6/1974 | Coopersmith et al. ...... 424/358 |
| 4,088,751 A | 5/1978 | Kenkare et al. ............... 424/47 |
| 4,110,426 A | 8/1978 | Barnhurst et al. ............. 424/46 |
| 4,439,416 A | 3/1984 | Cordon et al. ................. 424/47 |
| 4,839,081 A | 6/1989 | Church et al. ............... 510/159 |
| 5,505,937 A | 4/1996 | Castrogiovanni et al. ..... 424/64 |
| 5,863,524 A | 1/1999 | Mason et al. |
| 6,103,250 A | 8/2000 | Brieva et al. ................ 424/401 |
| 6,287,850 B1 | 9/2001 | Gott et al. ................... 424/401 |
| 6,344,205 B1 * | 2/2002 | Grimm et al. .............. 424/401 |
| 6,455,058 B1 * | 9/2002 | Sun et al. ................... 424/401 |
| 6,491,902 B2 | 12/2002 | Shefer et al. |
| 6,541,017 B1 | 4/2003 | Lemann et al. ............. 424/401 |
| 6,790,815 B1 * | 9/2004 | Bettiol et al. ............... 510/102 |
| 2003/0073607 A1* | 4/2003 | Smets et al. .................. 512/27 |

FOREIGN PATENT DOCUMENTS

| | | |
|---|---|---|
| EP | 0 027 730 | 10/1980 |
| EP | 0 586 929 A1 | 8/1993 |
| GB | 1357000 | 9/1971 |

* cited by examiner

*Primary Examiner*—Jyothsna Venkat
(74) *Attorney, Agent, or Firm*—Mathews, Shepherd, McKay & Bruneau, P.A.

(57) ABSTRACT

This invention relates to cosmetic applications for topical applications to the human skin. In particular, it relates to anhydrous cosmetic and dermatological compositions, with the capacity for self-warming or self-heating upon application. The self-warming or self-heating cosmetic compositions of the present invention comprise: (i) from about 0.1 to about 99% by weight of an anhydrous skin care preparation; and (ii) from about 0.01 to about 99% by weight of a heating agent selected from polyvinyl amine, polyalkyleneamine or polyalkyleneimine.

2 Claims, No Drawings

SELF-WARMING OR SELF-HEATING COSMETIC AND DERMATOLOGICAL COMPOSITIONS AND METHOD OF USE

BACKGROUND OF THE INVENTION

1. Field of the Invention

The present invention relates to self-warming or self-heating cosmetic compositions that are based upon the reaction of a polyvinyl amine or a polyalkyleneimines and water to provide the warmth sensation. The self-warming or self-heating cosmetic and dermatological composition is activated with moisture.

2. Description of the Related Art

Heat-producing cosmetic compositions produce a very pleasant sensation. These formulations are friendlier than the cold traditional products applied to the skin. Conventional systems developed for generating warmth have been described.

EP-A-27730 describes a cosmetic composition which may for example be a hair treatment or hand treatment composition and which generates heat on contact with water. In this application, heat generation is alleged to be provided by the presence of polyethylene oxides, polypropylene oxides, and derivatives thereof, and a 2 to 9 carbon atom alkaline glycol. It has been found that the formulation of compositions based on or containing significant amounts of propylene glycol needs to be very carefully controlled, since a number of propylene glycol based compositions suffer from product separation on storage.

EP-A-586929 describes a two pack system which generates heat on the addition of water, and produces a physiologically compatible salt that generates heat on mixture with water. Also contributing to the heat felt by the user on hydration of the product is the heat of hydration of polyethylene glycol.

GB-A-1357000 describes a topical cosmetic composition comprising an anhydrous polyol and an absorbent particulate filler material. Suitable polyols are said to include propylene glycol, glycerol, 1,3 butylene glycol, and polyethylene glycols having an average molecular weight of from 2 to 300 and from 1000 to 6000.

U.S. Pat. No. 6,287,580 discloses a self-warming cosmetic composition which delivers skin conditioning agents and is based upon a redox system of iron powder and a catalyst such as charcoal to provide the warmth. The system is activated with moisture and air. The self-warming composition is comprised of: (i) from about 0.1 to about 30% by weight of silicone oil or carboxylic ester as a skin conditioning agent; and (ii) from about 1 to about 95% by weight of a redox system based upon iron powder and a high surface area catalyst which is charcoal.

U.S. Pat. No. 4,839,081 discloses a two-stage chemically heated liquid soap composition dispensed as a cleansing composition for the face and hands. The heating is derived from a novel double reductant and single oxidant redox system. Preferred active parts of the redox system are hydrogen peroxide and a combination of sodium sulfite and ascorbic acid with a suitable catalyst. The other components of the composition may change in accordance with the desired cleansing properties of the composition.

U.S. Pat. No. 4,439,416 discloses a cosmetic preparation which is effective for providing a cosmetic product that is heated at time of use by the heat of an exothermic reaction, and a process for carrying out such heating. The self-heating cosmetic preparation is composed of at least two discrete parts particularly suitable for providing a heated cosmetic product at time of use has one part comprising a hydride and a second part comprising a reducible material adapted to react exothermically with said hydride on contact therewith, and a cosmetic base in which one of said parts is incorporated, whereby at time of use the parts combine and interact exothermically to issue as self-heated cosmetic preparation.

U.S. Pat. No. 4,110,426 describes nonaqueous compositions, especially cosmetic preparations such as shaving creams which are rendered self-heating by including iherein a compound containing at least one boron-oxygen-boron linkage, such as triethoxyboroxine, which reacts exothermically with water or other protic material.

U.S. Pat. No. 4,088,751 discloses a packaged self-heating cosmetic, such as a shaving cream, hand lotion, depilatory, facial, or a shampoo, including separate exothermically reactive reductant material, such as 2-thio-4-oxypyrimidine or thiohydantoin or derivatives thereof, and an oxidant, which reacts with the reductant, generating heat. Means are provided for dispensing the packaged reductant and oxidant from separate zones and bringing them into contact with each other so that they react and heat a pressurized shaving cream or other cosmetic product which are contacted by the exothermic reaction mixture. The reducing agent employed is preferably 2-thio-4-oxypyrimidine or its tautomer, 2-mercapto-4-hydroxypyrimidine, or alkyl-substituted derivative thereof, and the oxidizing agent is preferably aqueous hydrogen peroxide.

U.S. Pat. No. 3,250,680 relates to the use of finely divided solid adsorbent materials which are capable of exothermically reacting with water. Illustrative of these materials are silica gel, activated alumina and synthetic zeolites. U.S. Pat. No. 4,626,550 relates to similar heating systems with improved versions of zeolite based on the presence of potassium ions as replacement for some of the sodium ions. WO 93/08793 describes other exothermic agents which are reactive with water. The agents include kaolin, Fuller's Earth, china clay and bentonite.

U.S. Pat. No. 6,455,058 describes a composition and method for scalp treatment. The hair and scalp treatment contains an anti-dandruff agent such as salicylic acid, polyethylenimine (PEI) and an amphoteric surfactant. The anti-dandruff agent and PEI are incorporated in one formula to have a dual function of both hair and scalp treatments. PEI provides an effective hair conditioning ingredient. The composition is incorporated into either an aqueous or anhydrous solvent system. The anhydrous formulas have self-heating action whenever they are applied on wet hair.

The prior art of which applicant is aware does not set forth self-heating, or self-warming, anhydrous cosmetic products comprising of a polyvinyl amine or a polyalkyleneimines that imparts long lasting heating sensation in response to body moisture. Consumers expect a high level of sophistication in their cosmetic products and there is a need for products that can provide a warm sensation upon need and over an extended period of time, i.e., in response to body moisture.

SUMMARY OF THE INVENTION

Olfactory sensation, especially warm sensation, is often needed in various cosmetic preparations, such as shaving creams, hand lotions, body lotions, facial preparations, including masks, depilatories. The invention pertains cosmetic compositions in the form of sprays, sticks, strips, patches, shaving creams, hand lotions, body lotions, facial preparations, including masks, depilatories, creams, lotions, gels or pastes, which can evolve heat when in contact with moisture. This invention relates to cosmetic applications for topical applications to the human skin. In particular, it relates to anhydrous cosmetic compositions, with the capacity for self-warming or self-heating upon application.

The self-warming or self-heating cosmetic compositions of the present invention comprise:

(i) from about 0.1 to about 99% by weight of an anhydrous skin care preparation; and (ii) from about 0.01 to about 99% by weight of a heating agent selected from polyvinyl amine, polyalkyleneamine or polyalkyleneimine.

DETAILED DESCRIPTION

Self-warming or self-heating cosmetic and dermatological preparations of this invention include various compositions intended for application topically to the human body. Usually these are applied to the skin. They include face creams, body lotions, depilatories, tanning agents, antiperspirants, sun-screens, personal deodorants, shaving creams, makeup preparations, bath oils, facial treatments, astringents, after-shave lotions and many other related preparations.

The cosmetic preparations of this invention are made by simple conventional methods. The various constituents of the cosmetic portions of the preparations themselves can be combined in the normal manner and then, depending on the nature of the cosmetic, can be further formulated with the polyvinyl amine or the polyalkyleneimines being employed.

The self-warming or self-heating cosmetic compositions of the present invention comprise:

(i) from about 0.1 to about 99% by weight of an anhydrous skin care preparation; and (ii) from about 0.01 to about 99% by weight of a heating agent selected from polyvinyl amine, polyalkyleneamine or polyalkyleneimine.

Polyvinyl Amines

A preferred composition according to the present invention contains from about 0.1% to about 50%, more preferably from about 0.1% to about 30% by weight, of one or more polyvinyl amines having the formula

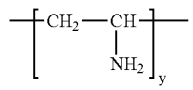

wherein y is from about 3 to about 10,000, preferably from about 10 to about 5,000, more preferably from about 20 to about 500. Polyvinyl amines suitable for use in the present invention are available from BASF under the name Lupasol®.

Optionally, one or more of the polyvinyl amine backbone —NH$_2$ unit hydrogens can be substituted by an alkyleneoxy unit having the formula:

—(R$_1$O)$_x$R$_2$ wherein R$_1$ is C$_2$–C$_4$ alkylene; R$_2$ is hydrogen, C$_1$–C$_4$ alkyl, and mixtures thereof; and x is from 1 to 50. In one embodiment of the present invention the polyvinyl amine is reacted first with a substrate which places a 2-propyleneoxy unit directly on the nitrogen followed by reaction of one or more moles of ethylene oxide to form a unit having the general formula:

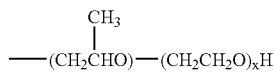

wherein x has the value of from 1 to about 50. Substitutions such as the above are represented by the abbreviated formula PO—EO—. However, more than one propyleneoxy unit can be incorporated into the alkyleneoxy substituent.

Polyalkyleneimines

A preferred composition of the present invention comprises a polyalkyleneimine having the formula:

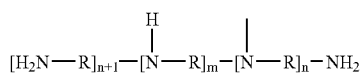

wherein the value of m is from 2 to about 700 and the value of n is from 0 to about 350. Preferably the compounds of the present invention comprise polyamines having a ratio of m:n that is at least 1:1 but may include linear polymers (n equal to 0) as well as a range as high as 10:1, preferably the ratio is 2:1. When the ratio of m:n is 2:1, the ratio of primary:secondary:tertiary amine moieties of —RNH$_2$, —RNH, and —RN moieties, is 1:2:1. R can be C$_2$–C$_8$ alkylene, C$_3$–C$_8$ alkyl substituted alkylene, and mixtures thereof. Preferably R is ethylene, 1,2-propylene, 1,3-propylene, and mixtures thereof, and more preferably ethylene. R radicals serve to connect the amine nitrogens of the backbone.

The polyamines of the present invention comprise homogeneous or non-homogeneous polyamine backbones, preferably homogeneous backbones. For the purpose of the present invention the term "homogeneous polyamine backbone" is defined as a polyamine backbone having R units that are the same such as, all ethylene. However, this definition does not exclude polyamines that comprise other extraneous units comprising the polymer backbone that are present due to an artifact of the chosen method of chemical synthesis. For example, it is known to those skilled in the art that ethanolamine may be used as an "initiator" in the synthesis of polyethyleneimines, therefore a sample of polyethyleneimine that comprises one hydroxyethyl moiety resulting from the polymerization "initiator" would be considered to comprise a homogeneous polyamine backbone for the purposes of the present invention.

For the purposes of the present invention the term "non-homogeneous polymer backbone" refers to polyamine backbones that are a composite of one or more alkylene or substituted alkylene moieties, for example, ethylene and 1,2-propylene units taken together as R units.

Other suitable polyamines for use in the present invention are generally polyalkyleneamines (PAA's), polyalkyleneimines (PAI's), preferably polyethyleneamine (PEA's), or polyethyleneimines (PEI's). Polyethyleneimines suitable for use in the present invention are available from BASF under the trade name Lupasol® such as Lupasol™ PR8515, having an average molecular weight of 1,800, Lupasol™ G20 Waterfree; Lupasol™ FG, Lupasol™ P, Lupasol™ PR971L; Lupasol™ PL; Lupasol™ SKA, and other Lupasol® products. Ethoxylated polyethyleneimines suitable for use in the present invention are available from BASF under the name Lupasol™ SC®-61B. A common polyalkyleneamine (PAA) is tetrabutylenepentamine. PEA's can be obtained by reactions involving ammonia and ethylene dichloride, followed by fractional distillation. The common PEA's obtained are triethylenetetramine (TETA) and tetraethylenepentamine (TEPA). Above the pentamines, such as, the hexamines, heptamines, octamines and possibly nonamines, the cogenerically derived mixture does not appear to separate by distillation and can include other materials such as cyclic amines and particularly piperazines.

Anhydrous Skin Care Material

The term "anhydrous composition" is understood to mean a composition comprising less than about 5% by weight of water with respect to the total weight of the composition, preferably from about 1% to about 2% of water, more preferably less than about 1% of water. Most preferably still, the composition does not comprise water at all. Suitable anhydrous skin care materials include high levels of nonpolar ingredients such as fats, oils, volatile and non-volatile linear and cyclic silicones, and waxes, which provide the cosmetics with a certain heavy, occlusive, feeling when applied to skin.

Linear and cyclic volatile silicones are available from various commercial sources including Dow Coming Corporation and General Electric. The Dow Corning volatile silicones are sold under the trade names Dow Coming 244, 245, 344, and 200 fluids. These fluids comprise octamethylcyclotetrasiloxane, decamethylcyclopentasiloxane, hexamethyldisiloxane, and mixtures thereof. Nonvolatile silicones, both water soluble and water insoluble, are also suitable as the oil component of the anhydrous composition provided they are nonpolar. Such silicones preferably have a viscosity of 10 to 600,000 centipoise, preferably 20 to 100,000 centipoise at 25 degree C. Suitable water insoluble silicones include dimethicone, amodimethicone, hexadecyl methicone, methicone, phenyl trimethicone, simethicone, dimethylhydrogensiloxane, vinyldimethicone, and mixtures thereof. Suitable water soluble silicones include dimethicone copolyol, provided it is lipophilic and/or nonpolar in character. Such silicones are available from Dow Coming as the 3225C formulation aid, Dow 190 and 193 fluids, or similar products marketed by Goldschmidt under the ABIL tradename. Silicone elastomers are generally three dimensional cross-linked chain polymers which have rubber-like properties. Silicone elastomers are known for use in both anhydrous and emulsion form cosmetics, and are known to provide unique feel and aesthetics to cosmetic formulas.

Also suitable as volatile oils for use in the anhydrous composition are various straight or branched chain paraffinic hydrocarbons having 5 to 40 carbon atoms, more preferably 8–20 carbon atoms. Suitable hydrocarbons include pentane, hexane, heptane, decane, dodecane, tetradecane, tridecane, and $C_{8-20}$ isoparaffins as disclosed in U.S. Pat. Nos. 3,439,088 and 3,818,105, both of which are hereby incorporated by reference. Preferred volatile paraffinic hydrocarbons have a molecular weight of about 70–225, preferably about 160 to about 190 and a boiling point range of about 30 to about 320, preferably 60–260 degrees C., and a viscosity of less than about 10 centipoise. at about 25 degrees C. Such paraffinic hydrocarbons are available from EXXON under the ISOPARS trademark, and from the Permethyl Corporation. Suitable $C_{12}$ isoparaffins such as isododecane are manufactured by Permethyl Corporation under the tradename Permethyl 99A. Various $C_{16}$ isoparaffins commercially available, such as isohexadecane (having the tradename Permethyl R), are also suitable. Transfer resistant cosmetic sticks of the invention will generally comprise a mixture of volatile silicones and volatile paraffinic hydrocarbons.

A wide variety of nonvolatile oils are also suitable for use in the anhydrous compositions of the invention. The nonvolatile oils generally have a viscosity of greater than about 10 centipoise at 25 degrees C., and may range in viscosity up to about 1,000,000 centipoise at about 25 degrees C. The nonpolar oil may be a variety of silicone or organic natural or synthetic oils.

Also suitable as the oil in the anhydrous composition are synthetic or semi-synthetic glyceryl esters, e.g. fatty acid mono-, di-, and triglycerides which are natural fats or oils that have been modified, for example, glyceryl stearate, glyceryl dioleate, glyceryl distearate, glyceryl trioctanoate, glyceryl distearate, glyceryl linoleate, glyceryl myristate, glyceryl isostearate, polyethylene glycol (PEG) castor oils, PEG glyceryl oleates, PEG glyceryl stearates, PEG glyceryl tallowates, and the like.

The anhydrous composition can comprise one or more waxy solids. Suitable waxes include animal, plant, mineral, and silicone waxes. Examples of such waxes are apple, avocado, bayberry, beeswax, candelilla, ceresin, cetyl esters, hydrogenated jojoba wax, microcrystalline, hydrolyzed beeswax, jojoba butter, jojoba esters, lanolin, mink, montan, organ, ouricury, oxidized beeswax, ozokerite, palm kernel, paraffin, PEG-beeswax, rice, shellac, polyethylene, and the like. Also suitable are silicone waxes such as stearyl dimethicone, behenoxydimethicone, silicone ester waxes such as those disclosed in U.S. Pat. No. 5,505,937, which is hereby incorporated by reference.

Various synthetic polymers are suitable for use as the nonpolar phase in anhydrous compositons, provided the synthetic polymers are lipophilic in character. Examples of such synthetic polymers include those made from ethylenically unsaturated monomers, for example, ethylene/propylene copolymers, acrylates, methacrylates, and the like.

The compositions of the invention can comprise a number of other ingredients which enhance the beneficial properties thereof, including water sensitive ingredients, humectants, polyols, preservatives, antioxidants, and the like.

Anhydrous polar ingredients, for example, mono- and difunctional alcohols such glycerin, propylene glycol, and the like, are known for their ability to improve formula aesthetics. Anhydrous cosmetic, pharmaceutical, or hygienic compositions have ingredients similar to those disclosed in U.S. Pat. Nos. 6,541,017, 6,344,205, and 6,103,250, each hereby incorporated by reference.

In general, the inventive composition is composed of two major ingredients: of a polyvinyl amine or a polyalkyleneimines and/or its derivatives and mixtures thereof and an anhydrous skin care preparation. The composition can include polyethylenimine in the amount of about 0.01% to about 99%, about 0.1% to about 50% or about 5.0% to about 30% by weight by total weight of the composition.

The self-warming of self-heating cosmetic compositions can include ingredients commonly employed in cosmetic compositions such as shaving cream, hand cleanser and facial cleanser compositions include soaps, synthetic detergents including foaming agents, foam boosters, and germicides; fatty alcohols and acids, fatty oils and mineral oils, pigments and fillers, thickeners, astringents, emollients, solubilizers, humectants, alkalizing agents, buffers and the like. Any or all of the foregoing ingredients as well as other conventional ingredients can be present in the composition of the present invention.

A method of self-warming or self-heating the skin comprises the steps of placing the self-warming or self-heating cosmetic compositions on the skin, wherein the composition evolves heat upon contact with moisture of the skin.

The invention can be further illustrated by the following examples thereof, although it will be understood that these examples are included merely for purposes of illustration and are not intended to limit the scope of the invention unless otherwise specifically indicated. All percentages, ratios, and parts herein, in the Specification, Examples, and Claims, are by weight and are approximations unless otherwise stated.

Self-Warming, or Self-Heating, Silicone Lotion

EXAMPLE 1

The anhydrous silicone lotion base utilized was a commercial product obtained from Medicia of Dayton, N.J. 30 grams of LUPASOL™ PR815, a polyethyleneimine having an average molecular weight of 1800 (commercially available from BASF Corporation) were added to 70 grams of the anhydrous silicone lotion and the composition is mixed well. 0.5 grams of the lotion were applied on the forearm and massaged well into the skin. A warm feeling was sensed in few seconds. The warmth sensation significantly increased after adding water on the treated area.

Self-Heating Cream-to Powder Anhydrous Makeup

EXAMPLE 2

The polyethyleneimine of the present invention can be incorporated in any anhydrous cosmetic formulation to create heat or warming sensation, for example, 10% of LUPASOL™ FG, a polyethyleneimine having an average molecular weight of 800 (commercially available from BASF Corporation) was incorporated in the following makeup cream formulation (Happi Magazine Formulary May 2003):

| Ingredients: | % Wt. |
| --- | --- |
| Phase A | |
| Permethyl 102A (Presperse) (isoeicosane) | 44.20 |
| Carnauba wax | 3.50 |
| Propylparaben USP (ISP) (propylparaben) | 0.20 |
| Phase B | |
| Sericite PHN (Presperse) (mica) | 40.00 |
| SP-29 UVS (Presperse) (bismuth oxychloride (and) silica (and) mica | 3.00 |
| Titanium Dioxide 3328 (Whittaker) (titanium dioxide) | 7.00 |
| Red Iron Oxide 7080 (Warner Jenkinson) (iron oxide) | 0.80 |
| Yellow Iron Oxide 7055 (Warner Jenkinson) (iron oxide) | 0.60 |
| Black Iron Oxide 7133 (Warner Jenkinson) | 0.30 |
| Phase C | |
| Amisol (Lucas Meyer) (lecithin (and) polysorate 20 (and) sorbitan laura) | 0.40 |

Procedure: In a suitable vessel, combine all ingredients of phase A and heat to 82° C. under Lightnin-type mixing. In a separate vessel, combine phase B in a ribbon-type blender to even dispersion. Add phase B to phase A under Lightnin-type mixing; mix to uniformity.

Add phase C and continue mixing. Add 10% LUPASOL™ FG and pour into appropriate containers at 70–75° C. 0.5 grams of the lotion were applied on the forearm and massaged well into the skin. A warm feeling was sensed in few seconds. The warmth sensation significantly increased after adding water on the treated area.

Self-Heating Moisturizing Body Gel

EXAMPLE 3

The polyethyleneimine of the present invention can be incorporated in any anhydrous cosmetic formulation to create heat or warming sensation, for example, 15% of LUPASOL™ PR8515, a polyethyleneimine having an average molecular weight of 2000 (commercially available from BASF Corporation) was incorporated in the following moisturizing body gel formulation (Happi Magazine Formulary May 2003):

| Ingredients: | % Wt. |
| --- | --- |
| Jeechem HPIB (Jeen) (dimethicone crosspolymer-3 (and) cyclomethicone (and) polyisobutene) | 86.50 |
| Jeescreen OMC (Jeen) (octyl methocycinnamate) | 7.50 |
| Jeescreen OS (Jeen) (octyl salicylate) | 5.00 |
| Fragrance 119147 (AFF International) | 1.00 |

Procedure: Combine the sunscreen phase with the fragrance and mix until uniform. Add this premix slowly to the Jeechem HPIB at room temperature and mix until uniform. Mix 85% of the moisturizing body gel formulation with 15% LUPASOL™ PR8515 and stir well. 0.5 grams of the lotion were applied on the forearm and massaged well into the skin. A warm feeling was sensed in few seconds. The warmth sensation significantly increased after adding water on the treated area.

Self-Heating Massage Oil

EXAMPLE 4

The polyethyleneimine of the present invention can be incorporated in any anhydrous cosmetic formulation to create heat or warming sensation, for example, 5% of LUPASOL™ PR8515, a polyethyleneimine having an average molecular weight of 2000 (commercially available from BASF Corporation) was incorporated in the following massage oil formulation (Happi Magazine Formulary September 2001):

| Ingredients: | % Wt. |
| --- | --- |
| Phase A | |
| Pureco HOS (Sunflower Oil) | 70.00 |
| Captex 350 (caprylic/capric/lauric triglyceride) | 7.00 |
| Soybean oil | 13.00 |
| Abil Wax (Goldschmidt) (cetyl dimethicone) | 2.00 |
| Phase B | |
| Captex 200 (propylene glycol dicaprylate/dicaprate) | 5.00 |
| Perfume | q.s. |
| Phase C | |
| Preservatives | q.s. |

Procedure: Weigh phase A ingredients into a vessel and stir at room temperature until even. Disperse phase B perfume and add to phase A with mixing. Add preservatives as needed. Combine 95% of the massage oil formulation with 5% LUPASOL™ PR8515 and mix well. 0.5 grams of the lotion were applied on the forearm and massaged well into the skin. A warm feeling was sensed in few seconds. The warmth sensation significantly increased after adding water on the treated area.

What is claimed is:

1. A topical self-warming or self-heating anhydrous skin care composition comprising:

from about 0.01% to about 99% by weight of an anhydrous skin care material, said anhydrous skin care material comprising a material selected from the group consisting of octamethylcyclotetrasiloxane, decamethylcyclopentasiloxane, hexamethyldisiloxane, dimethicone, amodimethicone, hexadecyl methicone, methicone, phenyl trimethicone, simethicone, dimethylhydrogensiloxane, vinyldimethicone, dimethicone copolyol and mixtures thereof; and from about 0.01% to about 99% by weight of a heating agent selected from the group consisting of polyvinyl amine and polyalkyleneamine.

2. The composition of claim 1 wherein the heating agent is polyethyleneamine.

* * * * *